United States Patent [19]

Dufresne et al.

[11] Patent Number: 4,723,048

[45] Date of Patent: Feb. 2, 1988

[54] PROCESS FOR DISMUTATION AND TRANSALKYLATION OF AROMATIC HYDROCARBONS IN THE PRESENCE OF A ZEOLITE CATALYST

[75] Inventors: Pierre Dufresne, Rueil Malmaison; Christian Marcilly, Houilles; Francis Raatz, Rueil Malmaison, all of France

[73] Assignee: Institut Francais Du Petrole, Rueil-Malmaison, France

[21] Appl. No.: 901,333

[22] Filed: Aug. 28, 1986

[30] Foreign Application Priority Data

Aug. 28, 1985 [FR] France .............................. 85 12916

[51] Int. Cl.$^4$ .............................................. C07C 5/22
[52] U.S. Cl. ..................................... 585/474; 585/475
[58] Field of Search ................................. 585/474, 475

[56] References Cited

U.S. PATENT DOCUMENTS

| | | | |
|---|---|---|---|
| 3,892,657 | 7/1975 | Wilhelm | 585/476 |
| 4,051,018 | 9/1977 | Knapik et al. | 208/139 |
| 4,131,536 | 12/1978 | Adams et al. | 208/139 |
| 4,175,031 | 11/1979 | Antos | 585/477 |

Primary Examiner—Curtis R. Davis
Attorney, Agent, or Firm—Millen & White

[57] ABSTRACT

The invention concerns an improved process for dismutation and transalkylation of alkylaromatic hydrocarbons in the presence of a catalyst consisting essentially of acid mordenite having a total $SiO_2/Al_2O_3$ molar ratio from 9 to 80 and a sodium content lower than 1% by weight, said catalyst containing at least one metal selected from group M formed of nickel, palladium and metals from group $I_B$ of the periodic classification of elements and containing at least one metal of group $IV_A$ of said classification.

The catalyst preferably contains from 30 to 99.9 % by weight of mordenite, from 0.005 to 25% by weight of a group M metal, from 0.05 to 10% by weight of a group $IV_A$ metal and optionally up to 50% by weight of a binding agent.

The invention is particularly useful for dismutation of toluene or transalkylation of toluene and of alkylaromatic hydrocarbons having at least 9 carbon atoms per molecule.

10 Claims, 5 Drawing Figures

FIG.1

PROCESS FOR DISMUTATION AND TRANSALKYLATION OF AROMATIC HYDROCARBONS IN THE PRESENCE OF A ZEOLITE CATALYST

The present invention concerns the catalytic conversion of aromatic hydrocarbons. More precisely, it concerns dismutation of alkyl aromatic hydrocarbons such as toluene, to produce benzene and xylenes, or transalkylation of alkylaromatic hydrocarbons such as toluene and trimethylbenzenes to produce xylenes. These reactions are conducted in the presence of a catalyst and generally the operating conditions are as follows: temperature from 250° to 550° C., preferably from 330° to 500° C.; pressure from 10 to 60 bars, preferably from 20 to 45 bars; feeding space velocity, expressed in grams of charge feed per gram of catalyst and per hour, from 0.1 to 10 and preferably from 0.5 to 4; hydrogen to hydrocarbons molar ratio from 2 to 20, preferably from 3 to 12.

The present invention has as an object the use of a particular catalyst which is very efficient for the dismutation of toluene and/or transalkylation of toluene and $C_9^+$ alkylaromatic hydrocarbons (i.e. having 9 or more carbon atoms per molecule).

The catalyst appears to be highly selective and shows improved activity and stability as compared with the catalysts of the prior art. This catalyst, ready for use, consists of a mordenite of the "wide pores" type i.e. whose main pores have a diameter ranging from about 7 to about 10 Angströms, having a $SiO_2/Al_2O_3$ molar ratio from 9 to 80, preferably from 12 to 60 and more preferably from 20 to 50, containing less than 1% by weight and preferably less than 0.5% of sodium, and also containing, on the one hand, one or more transition metals selected from the group consisting of metals from group $I_B$ and VIII of the periodic classification of elements (Handbook of Chemistry and Physics 37th edition 1955-56 pages 392-393) and preferably selected from nickel, silver and palladium, and, on the other hand one or more metals from group $IV_A$, particularly germanium, tin and lead.

BACKGROUND OF THE INVENTION

Many dismutation and transalkylation catalysts whose main constituent is mordenite have already been described in the prior art. The type of mordenite used generally is a so-called "wide pores" mordenite i.e. a mordenite whose pores have a diameter of about 7 Angströms, said diameter being of about 8 to 10 Angströms in the catalyst ready for use, as disclosed in the U.S. Pat. No. 3,506,731 where mordenite is used in hydrogen form or in the two French patent applications No. 2 329 619 and 2 367 533 to the applicant.

Also U.S. Pat. No. 3,281,483 mentions mordenites essentially exchanged with silver or nickel ions; U.S. Pat. No. 3,780,121 mentions a mordenite exchanged with metal ions from group $I_B$ of the periodic classification of elements (copper, silver) which is characterized by a $SiO_2/Al_2O_3$ molar ratio from 12 to 80; U.S. Pat. No. 3,629,351 also concerns a mordenite containing metal ions from groups $I_B$, $V_A$, $VI_A$, $II_A$ and VIII of the periodic classification of elements, and, finally, U.S. Pat. No. 3,476,821 discloses the use of a mordenite containing a sulfurized metal from group VIII and having preferably a $SiO_2/Al_2/O_3$ molar ratio higher than 20.

According to the invention, the zeolite used as basic material for preparing the catalyst is a sodium-containing mordenite pertaining to the category of the so-called "wide pores" mordenites, i.e. mordenites whose main pores have a diameter from about 7 to 10 Angströms, or "small pores" mordenites, i.e. mordenites whose main pores have a diameter of about 4 to 6 Angströms, in sodic form. The mordenite used for manufacturing the catalysts described in the examples is in powder form or extruded in sodic form, sold under the trade name of zeolon by U.S. NORTON Company. It has an orthorhombic structure, a specific surface of about 400 to 500 $m^2.g^{-1}$, an adsorption capacity up to 13.5% by weight of water and a pore average diameter of about 7 Angströms. As a result of this pore opening, said mordenite can absorb in its structure microporosity, in two hours at 28° C. under 3333.05 Pa (25 mm Hg), from about 8 to 9% by weight of simple aromatic hydrocarbons such as benzene or toluene whose steric bulk is 6.8 Angströms, from about 7 to 8% by weight of orthoxylene (in two hours, at 28° C., under 933.26 Pa (7 mm Hg) or about 6 to 7% by weight of 2,2,4-trimethylpentane (isooctane) under 4933 Pa (37 mm Hg) at 28° C.

SUMMARY OF THE INVENTION

The present invention is an improved process for dismutation or transalkylation of alkylaromatic hydrocarbons conducted in the presence of a catalyst containing:

(a) at least one acid mordenite whose total $SiO_2/Al_2O_3$ molar ratio is from about 9 to about 80 and preferably from about 12 to about 60 and more advantageously from about 20 to about 50 and whose sodium content is lower than 1% by weight and preferably lower than 0.5% by weight and, more advantageously, lower than about 0.25% by weight, (b) at least one metal selected from the group formed of nickel, palladium and the metals of group $I_B$ of the periodic classification of elements, preferably selected from nickel, palladium and silver, (c) at least one metal selected from the metals of group $IV_A$ of the periodic classification of elements, preferably selected from tin, lead and germanium.

The catalyst used according to the invention preferably contains from 30 to 99.9% by weight of mordenite and, very advantageously, from 50 to 99.5%.

In order to prepare the catalyst according the invention, the major part of the sodium ions must be extracted from the mordenite; preferably the mordenite must not contain more than 1% by weight of sodium ions, more preferably not more than 0.5% by weight of sodium ions.

A first method consists of first replacing the sodium ions by ammonium ions, for example at a temperature from 0° to 120° C., by means of one or several successive ion exchange reactions.

A second method consists of subjecting the solid to one or several successive treatments with a solution of an inorganic acid such as HCl, $H_2SO_4$ or $HNO_3$ for example, at a concentration ranging for example from 0.3 to about 8M, for about 30 minutes to 24 hours, at a temperature from 20° C. to 120° C. When using this last method, simultaneously with the ionic exchange, i.e. the replacement of sodium by protons, a reaction of aluminum extraction from the alumino-silicate structure takes place which results in an increase of the $SiO_2/Al_2O_3$ molar ratio of the latter.

A third method consists of using a combination of the two preceding methods; for example one or several ionic exchange steps are conducted with a solution of an ammonium salt and then the solid is subjected to one or several treatments in acid medium such as precedingly described. It is also possible to perform the treatments in acid medium before the one or more ionic exchanges.

After removal of the major part of the sodium by one of the above-described techniques and in order to improve its acid properties and hence its performance, the zeolite carrier used in the invention is subjected to a roasting step in the presence of steam (called wet roasting) at a temperature from 300° to 850° C., preferably from 400° to 800° C., more preferably from 450° to 750° C., for a period from 15 minutes to one week, preferably from 30 minutes to 10 hours. The steam partial pressure ranges from 0.02 to 5 atmospheres (0.002–0.50 megaPascals (MPs)). This treatment results, as precedingly, in an aluminum extraction from the alumino-silicate structure and hence in an increase of the $SiO_2/Al_2O_3$ molar ratio of the latter but, in contrast with the treatments in acid medium whereby the so-extracted aluminum is removed from the structure, the wet roasting steps maintain the extracted aluminum in the channels of the zeolite, so that the total $SiO_2/Al_2O_3$ ratio of the solid does not change significantly.

The roasting of mordenite free of sodium in the presence of steam has been known for a long time and has been disclosed particularly in U.S. Pat. Nos. 3,506,400 and 3,551,353 and in the paper of CHEN and SMITH, Inorg. Chem. 1976, 15 p. 295.

After said first roasting, it is possible and even preferable to proceed to an etching in acid medium of the same type as those above described, so as to remove the major part of the aluminum extracted from the aluminosilicate structure but still present in the zeolite channels.

Each of the treatments described here, either by roasting in wet air or by acid etching, results in an increase of the silica content of the alumino-silicate structure but, as already stated, only the acid etching makes possible increasing the total $SiO_2/Al_2O_3$ ratio of the zeolite.

The desired values, according to the invention, for the total $SiO_2/Al_2O_3$ molar ratio of the zeolite may thus be obtained by proceeding to one or several successive cycles of wet air roasting-acid etching. When a single roasting in wet air is performed, it is preferably followed with an acid-etching so as to reach a total $SiO_2/Al_2O_3$ molar ratio preferably of at least 12. On the contrary, when several roastings in wet air are performed, the last treatment to which the zeolite is subjected may be either the roasting or the treatment in acid medium. The use of alternate cycles of treatments by wet air roasting-acid etching has also been disclosed in U.S. Pat. No. 3,551,353, G.B. Pat. No. 1,061,847 and in the papers of CHEN and SMITH Inorg. Chem. 1976, 15, p. 295; of CHEN, J. Phys. Chem. 1976, 80, p. 60 and, OLSON and ROLLMANN, Inorg. Chem. 1977, 16, p. 651.

The next step consists of introducing at least one of the transition elements pertaining either to group $I_B$ of the periodic classification, particularly silver or to group VIII of the same classification, particularly Ni and Pd. The one or more desired metals (silver, nickel or palladium) may be introduced either by impregnation of the dry solid or preferably by ionic exchange. When the catalyst contains two or three metals from silver, nickel and palladium, these metals may be either introduced all in the same manner or by identical methods for two of them and a different one for the third. When proceeding by ionic exchange technique the following ions of metals will be preferably used:

$Ag^+$ or $Ag(NH_3)_2^+$, $Ni^{2+}$ or $Ni(NH_3)_n^{2+}$ wherein n=2, 4 or 6,
$Pd^{2+}$ or $Pd(NH_3)_4^{2+}$.

The acetates of these metals may also be advantageously used for the exchange operation when the latter is performed on a mordenite of acid form, i.e. a mordenite wherein the most part of the compensation cations are $H^+$ ions. Several successive exchanges may be necessary to introduce the required amount of metals.

After introduction of the metal elements from groups $I_B$ and/or VIII of the periodic classification, the solid obtained is washed, filtered and dried for a period varying from a few minutes to a few days, at a temperature from about 80° to 200° C. according to the drying period, the longer drying steps being performed preferably at the lower temperatures. The product is then roasted in normal air or in dry air for about 30 minutes to 20 hours, preferably from about 1 to 10 hours, at a temperature from about 400° to about 700° C., preferably from about 450° to about 600° C.

Then the metal elements from group $IV_A$ of the periodic classification may be introduced. This operation is preferably performed by means of organic complexes wherein said metals are present, preferably at an oxidation degree from 0 to 2, for example. From the 3 metals of group $IV_A$ which are convenient for the present invention, i.e. germanium, tin and lead, the two preferred metals are tin and lead. Among the many possible complexes for introducing these metals, it is preferred to use the alkyl metals and particularly alkyl tin and alkyl lead. For example for tin there can be mentioned: tetramethyltin, tetraethyltin, tetrapropyltin, tetrabutyltin, dimethyltin dichloiide and dibutyltin dichloride and for lead, tetraethyl lead which is a product of large consumption.

The selected organic complexes are dissolved in aqueous or organic solutions, placed in neutral or reducing atmosphere, in contact with the mordenite produced by the above-described treatments and the whole is heated for several minutes to several days, preferably about from 5 minutes to about 72 hours, at a temperature from about 0 to about 150° C., in liquid phase, up to the decomposition of the desired complex amount. Almost always the decomposition of the organic complex is speeded up by the presence of precedingly deposited metal elements, particularly silver, nickel or palladium. It has however been observed, according to the present invention, that the decomposition velocity of these complexes on the exchanged mordenites roasted in air is low, particularly for mordenite exchanged with nickel, and that it may be preferable to previously reduce the solid in the presence of a reducing gas, particularly hydrogen or a gas of high hydrogen content, at a temperature from about 300° to 700° C., preferably from about 400° to 600° C., for about 30 minutes to 48 hours. Such a reduction very substantially increases the decomposition rate of the organic complex of metal from group $IV_A$ and hence the rate of fixation of the element on the carrier.

The total content of ions of transition metals from group $I_B$ (particularly Ag) or VIII (particularly Ni, Pd)

in mordenites may be from 0.005 to 25% by weight, the preferred content being as follows: 0.1 to 21% by weight for silver, 0.1 to 3.5% by weight for nickel and 0.005 to 2% by weight for palladium.

The total content of ions of metals from group $IV_A$ (Ge, and particularly Sn and Pb) in acid mordenites may be about 0.05 to 10% by weight, the preferred content being about 0.1 to 4% by weight.

In the present invention the catalyst is preferably used as pellets, aggregates, extrudates or balls. The shaping of the catalyst may be performed in the absence of a binding agent. It may also be performed before or after the exchange operations by using a binding agent which may be selected from the conventional binders such as clays, aluminas, silica, and/or silica-aluminas. The preferred binders according to the invention are clays and/or aluminas, used for example in a proportion of 3 to 50% by weight, preferably 5 to 40% by weight.

The catalyst prepared according to the present invention exhibit clearly improved catalytic properties as compared with the conventional catalysts for dismutation of toluene to benzene and xylenes and transalkylation of toluene by trimethylbenzenes. The catalysts conventionally used for these operations, which are acid mordenites exchanged with metals from group $I_B$, particularly silver, or from group VIII, particularly nickel, suffer from two major disadvantages: an insufficient selectivity, which results in a slight hydrogenation and degradation of the aromatic compounds to lighter saturated products, and an insufficient stability over time, which is problematic on the industrial scale. The catalysts according to the present invention result in very substantial improvements in these two respects: the loss of benzene rings at each passage into the reactor is thus divided by a factor from about 2 to about 20 and the stability, versus time, of the catalyst, measured for example by the time in days corresponding to an increase of 30° C. to maintain the toluene conversion to 40%, is multiplied by a factor of about 1.5 to 4.

The catalyst used according to the present invention, when it is withdrawn from the test unit after a test of several weeks, contains from about 0.5 to 4% by weight of coke. This coke may be easily removed by slow combustion in air of reduced oxygen content, up to a temperature of 550° C. The so-regenerated catalyst recovers the major part of its initial catalytic properties.

BRIEF DESCRIPTION OF THE DRAWINGS

The activities of the various catalysts prepared in the following examples are illustrated in FIGS. 1 and 2.

Curves a, b and d are those of catalyst A to D and curves g, h and i are those of tin-containing catalysts F to I.

EXAMPLES

The following examples illustrate the invention and must not be considered as limiting the scope thereof.

Examples 1 to 4 concern the preparation of acid mordenites having different $SiO_2/Al_2O_3$ molar ratios, used as reference catalysts $A_o$ to $D_o$. Examples 5 to 9 concern the preparation of nickel-containing catalysts of reference A to D (comparative example). Examples 10 to 15 concern the preparation of the catalysts according to the invention. Examples 16 concerns the preparation of tin-containing reference catalysts L, N, O and P (comparative example). Examples 17 to 23 concern the use of the catalysts in vapour phase toluene dismutation.

EXAMPLE 1

Preparation of an acid mordenite having a total $SiO_2/Al_2O_3$ molar ratio of 10.6.

900 g of sodium-containing mordenite (zeolon 900 Na) as extrudates of 1.587 mm (1/16th inch), sold on the trade by U.S. NORTON Cy, are subjected to two ion exchanges steps in ammonium nitrate solution in the following conditions:

Solution volume: 3.6 liters,
$NO_3NH_4$ concentration of the solution: 2M,
Exchange time: 1 hour,
Exchange temperature: T=90° C.

After each exchange, the solid is washed in 1.8 liter of distilled water for 20 minutes at 20° C.

At the end of these operations, the product is dried at 120° C. in a stove for 3 hours. The resultant solid is roasted for 2 hours at 550° C. in a stream of 180 liters per hour of wet air, containing 50% by volume of steam.

The mordenite in hydrogen form ($M_1$) obtained after said roasting step is again subjected to a ion exchange in an ammonium nitrate solution, in the same conditions as above described. It is then filtered, washed with distilled water as precedingly, dried at 120° C. and then roasted for 2 hours at 500° C. in dry air.

The two essential characteristics of said product ($M_2$) are:

Total $SiO_2/Al_2O_3$ molar ratio=10.6
Residual sodium % by weight=0.22.

This product ($M_2$) is called catalyst $A_o$ in the following tests.

EXAMPLE 2

Preparation of an acid mordenite having a $SiO_2/Al_2O_3$ total molar ratio of 14.6.

A new amount of sodium-containing mordenite, called zeolon 900 Na, is subjected to the treatment described in example 1, in order to prepare mordenite of hydrogen form ($M_1$).

The mordenite of hydrogen form ($M_1$), obtained by roasting in wet air as described in example 1, is dipped into 9 liters of 0.6M solution in hydrochloric acid and is treated for 2 hours at 90° C. in said solution.

After washing for 10 minutes in 5.4 liters of distilled water, followed by a filtration, the product is dried at 120° C. for 2 hours and then divided into 3 parts of identical weights.

The two essential characteristics of the product ($M_3$) are:
$SiO_2/Al_2O_3$ total molar ratio = 14.6
Residual sodium % by weight = 0.20

This product ($M_3$) is called catalyst $B_o$ in the following tests.

EXAMPLE 3

Preparation of an acid mordenite having a $SiO_2/Al_2O_3$ total molar ratio of 25.2.

Two of the three parts, i.e. 600 g of acid mordenite ($M_3$) obtained in example 2, are subjected to roasting in wet air in conditions comparable with those of example 1, except that temperature is brought to 600° C.

The obtained solid is dipped into 3.6 liters of normal HCl aqueous solution and is treated for 2 hours at 90° C. in said solution.

After washing for 10 minutes in 3.6 liters of distilled water at 20° C., the solid is dried at 120° C. for 2 hours.

The two essential characteristics of said acid mordenite ($M_4$) are:
$SiO_2/Al_2O_3$ total molar ratio = 25.2
Residual sodium % by weight = 0.11

This product ($M_4$) is called catalyst $C_o$ in the following tests.

EXAMPLE 4

Preparation of an acid mordenite having a $SiO_2/Al_2O_3$ total molar ratio of 58.6

300 g of acid mordenite ($M_4$) obtained in example 3 are subjected to a roasting in wet air in conditions comparable with those of example 1, except that the temperature is brought to 650° C.

The resultant solid is dipped into 1.8 liter of 2N hydrochloric acid aqueous solution and is treated for two hours at 90° C. in said solution.

The solid is then washed, filtered and dried as in example 2. The two essential characteristics of the obtained acid mordenite ($M_5$) are:
Total $SiO_2/Al_2O_3$ molar ratio = 58.6
Residual sodium % by weight = 0.09

This product ($M_5$) is called catalyst $D_o$ in the following tests.

EXAMPLE 5

Preparation of Ni—M2 reference catalyst A 100 g of acid mordenite ($M_2$) of example 1 are dipped and stirred in a volume of 900 cc of 0.5M nickel acetate aqueous solution at 20° C. for 24 hours.

The obtained solid is washed with distilled water, filtered and dried at 120° C. for a night. It is roasted in very dry air at 500° C. for 2 hours.

The so-obtained catalyst A has a nickel content of 1.81% by weight.

EXAMPLE 6

Preparation of Ni—M3 reference catalyst B 100 g of acid mordenite ($M_3$) of example 2 are subjected to the same treatments as described in example 5. The so-obtained catalyst B has a nickel content of 2.11% by weight.

EXAMPLE 7

Preparation of Ni—M4 reference catalyst C 100 g of acid mordenite ($M_4$) of example 3 are subjected to the same treatments described in example 5.

The so-obtained catalyst C has a nickel content of 1.10% by weight.

EXAMPLE 8

Preparation of Ni—M5 reference catalyst D.

100 g of acid mordenite ($M_5$) of example 4 are subjected to the same treatments as described in example 5.

The resultant catalyst D has a nickel content of 0.43% by weight.

EXAMPLE 9

Preparation of Pd—M4 reference catalyst E 100 g of acid mordenite ($M_4$) of example 3 are dipped into 500 cc of a solution containing 0.15 g of palladium as tetrammine palladium chloride $Cl_2Pd(NH_3)_4$, and 100 g of ammonium nitrate.

The mixture is stirred for 24 hours at 20° C.

At the end of this treatment the solid is washed with distilled water, filtered, dried at 120° C. for a night, then roasted in very dry air at 500° C. for 2 hours.

The resultant catalyst E has a palladium content of 0.1% by weight.

EXAMPLE 10

Preparation of catalyst F (Sn—Ni—M2)

50 g of catalyst A (Ni—M2) of example 5 are reduced in the presence of hydrogen at 500° C. for 2 hours. They are then placed at room temperature in a confined vessel scavenged with hydrogen and then contacted with 250 cc of a solution of n-heptane wherein are dissolved 2 grams of tin as tetramethyltin $(CH_3)_4Sn$. The whole is brought to boiling temperature and maintained at reflux for 2 hours.

The solid is then filtered, washed twice with n-heptane at room temperature for 20 minutes, then dried at 150° C. for 5 hours in a stove.

The resultant catalyst F contains 0.43% by weight of tin, which corresponds to a tin fixation rate of 21.5%.

EXAMPLE 11

Preparation of catalyst G (Sn—Ni—M3)

50 g of catalyst B of example 6 are subjected to a treatment identical to that described in example 10.

The resultant catalyst G contains 0.39% by weight of tin, which corresponds to a tin fixation rate of 19.5%.

EXAMPLE 12

Preparation of catalyst H (Sn—Ni—M4)

50 g of catalyst C of example 7 are subjected to a treatment identical to that described in example 10.

The resultant catalyst H contains 0.33% by weight of tin, which corresponds to a tin fixation rate of 16.5%.

EXAMPLE 13

Preparation of catalyst I (Sn—Ni—M5)

50 g of catalyst D of example 8 are subjected to a treatment identical to that described in example 10.

The resultant catalyst I contains 0.28% by weight of tin, which corresponds to a tin fixation rate of 14%.

EXAMPLE 14

Preparation of catalyst J (Pb—Ni—M4)

50 g of catalyst C of example 7 are reduced in the presence of hydrogen, at 500° C. for 2 hours. They are then placed at room temperature in a closed vessel scavenged with hydrogen and then contacted with 250 cc of n-heptane solution wherein 5 grams of lead, as tetraethyl lead ($C_2H_5)_4Pb$, are dissolved. The whole is brought to boiling and maintained at reflux for 2 hours.

The solid is then filtered, washed twice with n-heptane at room temperature for 20 minutes, then dried at 150° C. for 5 hours in a stove.

The so-obtained catalyst J contains 1.55% by weight of lead, which corresponds to a lead fixation rate of 31%.

EXAMPLE 15

Preparation of catalyst K (Sn—Pd—M4)

50 g of catalyst E of example 9 are subjected to a treatment similar to that described in example 10, except with respect to the reduction temperature which is limited to 450° C. and the tin amount initially used in n-heptane which is only 0.275 g.

The so-obtained catalyst K contains 0.52% by weight of tin, which corresponds to a tin fixation rate of 95.0%.

EXAMPLE 16

Preparation of catalysts L, N, O, P (Sn—$M_x$)

Tin is deposited on acid mordenites $M_2$ to $M_5$ prepared according to the above-described methods of examples 1 to 4, previously roasted at 500° C. in dry air. Mordenites $M_2$ to $M_5$ are "dry" impregnated, without excess of solution, by a tetramethyltin $(CH_3)_4Sn$ solution in n-heptane.

The concentration of tetramethyltin solution in n-heptane is so-selected as to fix the tin amounts mentioned hereinafter in Table 1 for each of the catalysts essentially consisting of mordenites $M_2$ to $M_5$.

Solids Sn—$M_2$, Sn—$M_3$, Sn—$M_4$, Sn—$M_5$, obtained after impregnation, are dried at 150° C. for 5 hours in a stove. The characteristics of the resultant catalysts L, N, O, P are reported in Table 1.

All the catalysts of examples 1 to 16, whose characteristics are summarized in Table 1, have been tested and compared in a test of toluene dismutation.

TABLE 1

| Catalyst | Formula | $SiO_2/Al_2O_3$ | % b.w. Na | % b.w. Ni | % b.w. Pd | % b.w. Sn | % b.w. Pb |
|---|---|---|---|---|---|---|---|
| $A_o$ | $M_2$ | 10.6 | 0.22 | — | — | — | — |
| $B_o$ | $M_3$ | 14.6 | 0.20 | — | — | — | — |
| $C_o$ | $M_4$ | 25.2 | 0.11 | — | — | — | — |
| $D_o$ | $M_5$ | 58.6 | 0.009 | — | — | — | — |
| A | Ni—$M_2$ | 10.6 | 0.22 | 1.81 | — | — | — |
| B | Ni—$M_3$ | 14.6 | 0.20 | 2.11 | — | — | — |
| C | Ni—$M_4$ | 25.2 | 0.11 | 1.10 | — | — | — |
| D | Ni—$M_5$ | 58.6 | 0.09 | 0.43 | — | — | — |
| E | Pd—$M_4$ | 25.2 | 0.11 | — | 0.10 | — | — |
| F | Sn—Ni—$M_2$ | 10.6 | 0.22 | 1.81 | — | 0.43 | — |
| G | Sn—Ni—$M_3$ | 14.6 | 0.20 | 2.11 | — | 0.39 | — |
| H | Sn—Ni—$M_4$ | 25.2 | 0.11 | 1.10 | — | 0.33 | — |
| I | Sn—Ni—$M_5$ | 58.6 | 0.09 | 0.43 | — | 0.28 | — |
| J | Pb—Ni—$M_4$ | 25.2 | 0.11 | 1.10 | — | — | 1.55 |
| K | Sn—Pd—$M_4$ | 25.2 | 0.11 | — | 0.10 | 0.52 | — |
| L | Sn—$M_2$ | 10.6 | 0.22 | — | — | 0.42 | — |
| N | Sn—$M_3$ | 14.6 | 0.20 | — | — | 0.38 | — |
| O | Sn—$M_4$ | 25.2 | 0.11 | — | — | 0.33 | — |
| P | Sn—$M_5$ | 58.6 | 0.09 | — | — | 0.28 | — |

EXAMPLE 17

Description of the catalytic test of toluene dismutation in vapour phase

The tests are conducted in the following conditions:
Total pressure: 20 bars (2 MPa)
Molar ratio $H_2$/toluene=4
1st series of conditions to compare the activity of the catalysts at low conversion rate
WWH=toluene weight feeding rate per gram of catalyst and per hour: 5 $h^{-1}$
Variable temperature selected to obtain a total conversion lower than 15%.
2nd series of conditions for comparing the selectivity of the catalysts at high conversion rate
WWH=1.5 $h^{-1}$
Variable temperature selected to obtain a total conversion ranging from 40 to 50%.

A test of catalyst accelerated ageing is performed, after determination of its activity and of its selectivity, by increasing the temperature to 520° C. for 6 hours at WWH=5 $h^{-1}$. The activity of the "aged" catalyst, then determined in the above-described conditions, makes possible the evaluation of the stability, versus time, of the catalyst.

The activity of the catalyst is estimated by the temperature necessary to reach a conversion equal to 10%, extrapolated from various experimental points obtained in the first series of conditions and that necessary to obtain a conversion equal to 45% in the second series of conditions.

The selectivity of the catalyst is estimated from the total content of saturated hydrocarbons containing 1 to 9 carbon atoms (practically the most part of these compounds have from 1 to 7 carbon atoms) obtained at high conversion rate (45%). The higher this content, the lower the selectivity. The selectivity may also be evaluated from the percent values of the various light saturated hydrocarbons obtained in the $C_1$-$C_4$ cut.

The stability of the catalyst is estimated from the temperature increase required to recover, after the catalyst accelerated ageing, the conversion rate obtained before said ageing, in the two series of conditions previously described (corresponding respectively to 10 and 45% of total conversion).

EXAMPLE 18

Comparison of reference catalysts A to D

Figure 1:
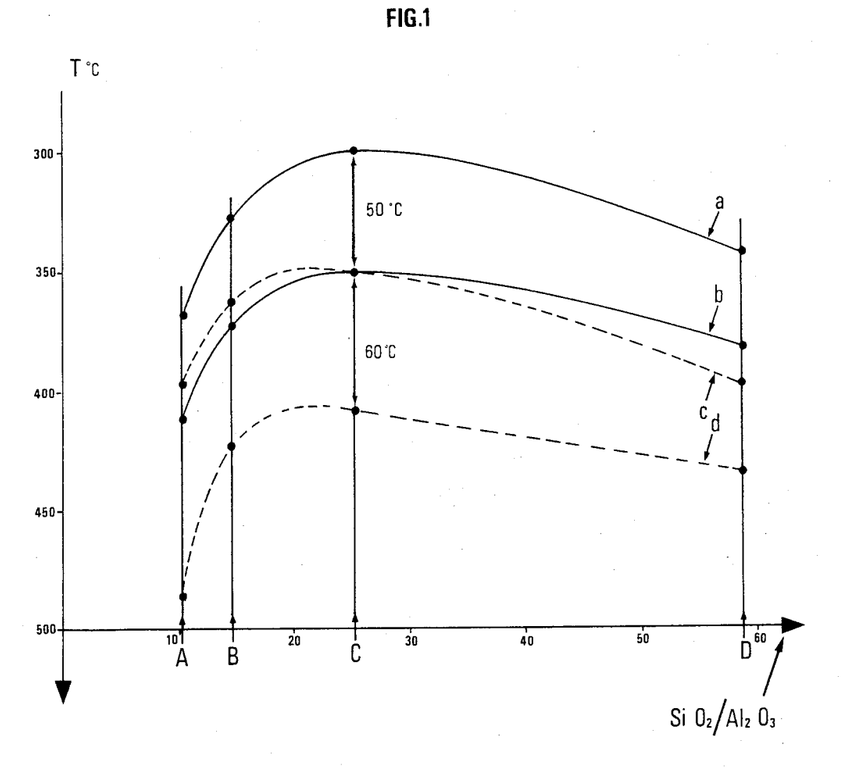
FIG. 1 shows the activities and stabilities of catalysts A to D versus temperature for a 10% conversion (curves a and c) and for a 45% conversion (curves b and d) before ageing (curves a and b) and after ageing (curves c and d).

The activities at low conversion rate (10%) and at high conversion rate (45%) of catalysts A to D are compared in a temperature diagram plotted against $SiO_2/Al_2O_3$ ratio (T(°C.)=f($SiO_2/Al_2O_3$)) shown in FIG. 1.

Figure 2:
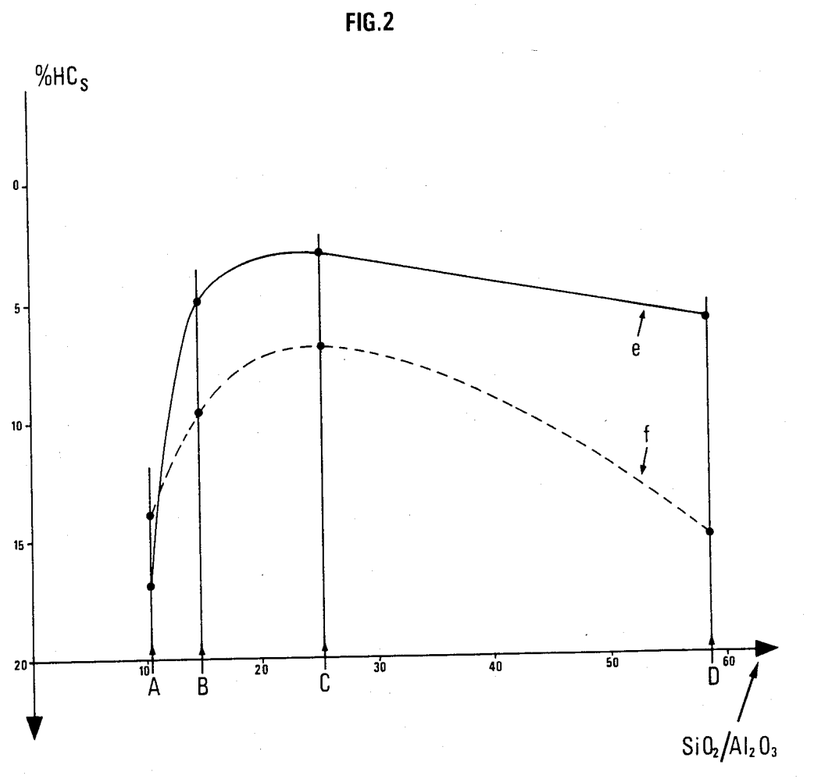
FIG. 2 shows the selectivities of catalysts A to D for a 45% conversion rate before ageing (curve e) and after ageing (curve f). On the "y" axis the ordinates represent the percentage of obtained $C_1$–$C_9$ saturated hydrocarbons (% $HC_s$).

The selectivities at high conversion rate (45%) of catalysts A and D are plotted in a diagram of the percentage of formed saturated hydrocarbon versus the $SiO_2/Al_2O_3$ ratio (%($HC_s$)=f($SiO_2/Al_2O_3$)) shown in FIG. 2. Table 2 showing the distribution of $C_1$ to $C_4$ gases also gives informations on the selectivity.

The stability of the catalyst may be estimated in FIG. 1 by comparing the temperatures at which are obtained respective conversion rates of 10% and 45%, before ageing of the catalyst, to those obtained after ageing.

Thus the following main points are made apparent:

The activity and the selectivity improve when the $SiO_2/Al_2O_3$ ratio increases from 10 to a value ranging about from 20 to 35, then they slightly decrease for higher values, and progressively recover, for a ratio of about 50, a level close to that obtained for a value 10 of the ratio.

Table 2 indicates that the formed $C_1$-$C_4$ light hydrocarbons contain a high proportion of $C_1+C_2$, mainly after ageing of the catalyst. This is probably attributable to a parasitic hydrogenolysis reaction.

The stability of the various catalysts depends on the conversion level. Catalysts A and B of low $SiO_2/Al_2O_3$ ratios (lower than 15) have an excellent stability of low conversion rate but their stability at high conversion rate is clearly not so good. On the contrary, the catalysts of $SiO_2/Al_2O_3$ ratio higher than about 20 have the same stability, irrespective of the conversion rate: the observed deactivation after ageing corresponds to a temperature increase of about 50°–60° C.

TABLE 2

Percentages (by weight) of products and distribution of $C_1$ to $C_4$ ($C_4^-$) light saturated hydrocarbons at high conversion rate (45%) for catalysts A to D, before (be) and after (af) ageing.

| CATALYSTS | | % $C_4^-$ * | % $C_1 + C_2$ in $C_4^-$ | % $C_3$ in $C_4^-$ | % $C_4$ in $C_4^-$ |
|---|---|---|---|---|---|
| A | be | 12.0 | 30.5 | 37.6 | 32.9 |
|   | af | 3.1 | 68.2 | 23.6 | 8.2 |
| B | be | 4.3 | 31.2 | 46.9 | 21.9 |
|   | af | 8.5 | 81.5 | 14.5 | 4.0 |
| C | be | 1.3 | 19.2 | 48.4 | 32.4 |
|   | af | 5.8 | 67.9 | 26.8 | 5.3 |
| D | be | 3.9 | 39.6 | 33.1 | 27.3 |
|   | af | 14.6 | 89.1 | 7.6 | 3.3 |

* % by weight in the formed products

EXAMPLE 19

Figure 3:
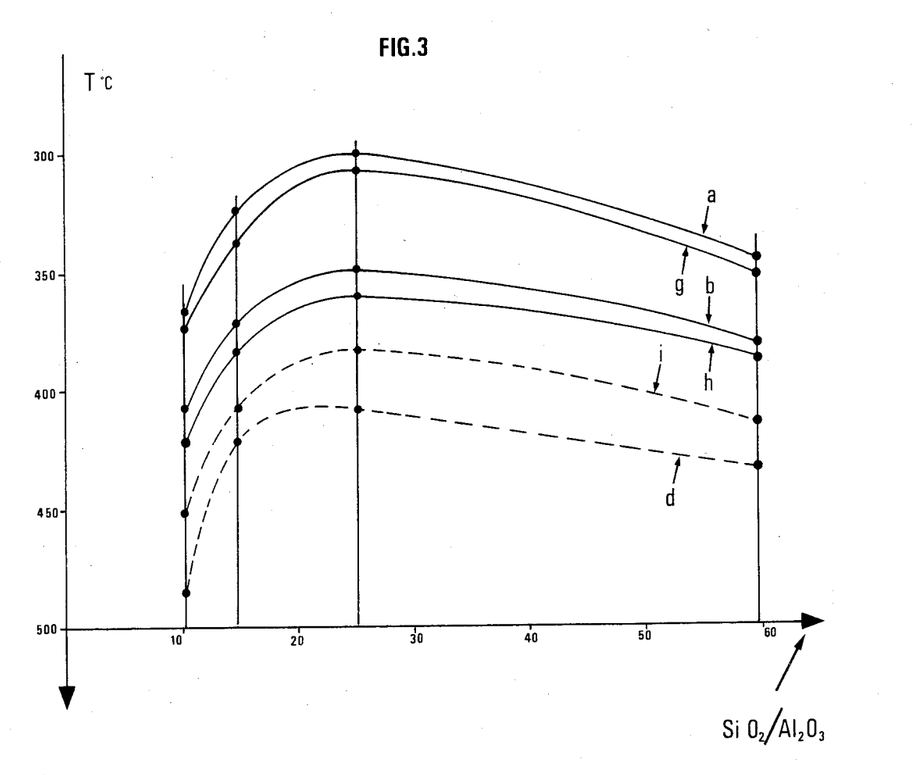
FIG. 3 shows the activities and stabilities of catalysts A to D and F to I versus temperature for a 10% conversion (curves a and g) and for a 45% conversion (curves b and h) before ageing and for a 45% conversion after ageing (curves i and d).

Comparison of catalysts F to I, containing tin and nickel, with reference catalysts A to D FIG. 3 shows that the introduction of tin in nickel-containing acid mordenites characterized by different $SiO_2/Al_2O_3$ molar ratios ranging from 10.6 to 58.6, always results in:

a slight decrease of the catalyst activity corresponding approximately to a necessary temperature increase of 10° C.

a clear improvement of the stability after accelerated ageing of the catalyst: the catalyst activity loss after ageing corresponds to a temperature increase of 50°–60° C. for reference catalysts A to D (Ni-mordenite) as compared with 20°–30° C. only, for catalysts F to I (Sn—Ni-mordenite).

Tables 3 and 4 indicate the yields of total formed $C_1$-$C_9$ saturated products, of the formed $C_1$-$C_4$ light saturated products, and the distribution of each of the $C_1$ to $C_4$ hydrocarbons in the $C_4^-$ ($C_1$-$C_4$) fraction. They show that the presence of tin provides for a considerable improvement of the selectivity of nickel-containing mordenites by highly reducing the production of non aromatic compounds.

Table 4 indicates that the proportion of formed $C_1+C_2$ in $C_4^{-1}$ light gases strongly decreases with catalysts F to I as compared with catalysts A to D (see Table 2) thus showing that tin modifies the nickel properties.

TABLE 3

Percentages (by weight) of produced $C_1$ to $C_9$ saturated hydrocarbons when using catalysts F to I as compared with the use of catalysts A to D before ageing (before) and after ageing (after) for a conversion rate of 45%.

| Catalysts | | % of formed $C_1$ to $C_9$ saturated HC | |
|---|---|---|---|
| $SiO_2/Al_2O_3$ | | before | after |
| 10.6 | A (Ni—$M_2$) | 17.1 | 14.0 |
|      | F (Sn—Ni—$M_2$) | 1.9 | 1.3 |
| 14.6 | B (Ni—$M_3$) | 5.1 | 9.5 |
|      | G (Sn—Ni—$M_3$) | 1.2 | 0.7 |
| 25.2 | C (Ni—$M_4$) | 3.0 | 7.0 |
|      | H (Sn—Ni—$M_4$) | 0.5 | 0.4 |
| 58.6 | D (Ni—$M_5$) | 5.9 | 15.6 |
|      | I (Sn—Ni—$M_5$) | 0.9 | 0.7 |

TABLE 4

Percentage (by weight) and distribution of produced $C_1$ to $C_4$ ($C_4^-$) light saturated hydrocarbons at high conversion rate (45%) for catalyst F to I, before (be) and after (af) ageing.

| CATALYSTS | | % $C_4^-$ | % $C_1 + C_2$ in $C_4^-$ | % $C_3$ in $C_4^-$ | % $C_4$ in $C_4^-$ |
|---|---|---|---|---|---|
| F | be | 1.5 | 25.3 | 50.6 | 24.1 |
|   | af | 1.1 | 22.6 | 52.1 | 25.3 |
| G | be | 1.0 | 16.7 | 59.3 | 24.0 |
|   | af | 0.6 | 10.3 | 68.2 | 21.5 |
| H | be | 0.4 | 6.1 | 76.3 | 17.6 |
|   | af | 0.3 | 5.2 | 77.8 | 17.0 |
| I | be | 0.7 | 12.4 | 69.1 | 18.5 |
|   | af | 0.5 | 9.5 | 72.4 | 18.1 |

EXAMPLE 20

Comparison of catalysts E (Pd-mordenite) and K (Sn—Pd-mordenite)

Table 5 hereinafter shows the main characteristics of activity, selectivity and stability of the two catalysts, before (be) and after (af) ageing.

The percentages of the products are expressed by weight and the distribution of $C_1$ to $C_4$ ($C_4^-$) light hydrocarbons is expressed in percent by weight of the $C_4^-$ fraction.

The results show that the palladium and tin-containing catalyst according to the present invention has an initial activity very close (although slightly lower) than the reference catalyst, but its selectivity and stability versus time are clearly improved.

EXAMPLE 21

Comparison of catalysts C (Ni-mordenite) and J (Pb—Ni-mordenite)

Table 6 hereinafter shows the main characteristics of activity, selectivity and stability of the two catalysts, before (be) and after (af) ageing.

The percentages of products are expressed by weight and the distribution of $C_1$ to $C_4$ ($C_4^-$) light hydrocarbons is expressed in percent by weight of the $C_4^-$ fraction.

The results show that the nickel and lead-containing catalyst according to the invention has an initial activity slightly lower than the reference catalyst but exhibits clearly improved selectivity and stability versus time.

TABLE 5

| CATALYSTS | | T° C. 10% Conversion | T° C. 45% Conversion | % $C_1$ to $C_9$ (*) | % $C_4^-$ (*) | % $C_1 + C_2$ in $C_4^-$ (*) | % $C_3$ in $C_4^-$ (*) | % $C_4$ in $C_4^-$ (*) |
|---|---|---|---|---|---|---|---|---|
| E(Pd—M$_4$) | be | 295 | 345 | 6.5 | 5.6 | 6.1 | 73.8 | 20.1 |
|  | af | 350 | 400 | 5.8 | 5.1 | 5.5 | 73.6 | 20.9 |
| K(Sn—Pd—M$_4$) | be | 300 | 350 | 0.8 | 0.7 | 5.1 | 74.4 | 20.5 |
|  | af | 315 | 370 | 0.7 | 0.6 | 4.5 | 75.1 | 20.4 |

(*)values corresponding to 45% conversion

TABLE 6

| CATALYSTS | | T° C. 10% Conversion | T° C. 45% Conversion | % $C_1$ to $C_9$ (*) | % $C_4^-$ (*) | % $C_1 + C_2$ in $C_4^-$ (*) | % $C_3$ in $C_4^-$ (*) | % $C_4$ in $C_4^-$ (*) |
|---|---|---|---|---|---|---|---|---|
| C(Ni—M$_4$) | be | 300 | 350 | 3.0 | 1.3 | 19.2 | 48.4 | 32.4 |
|  | af | 350 | 410 | 7.0 | 5.8 | 67.9 | 26.8 | 5.3 |
| J(Pb—Ni—M$_4$) | be | 315 | 360 | 0.8 | 0.6 | 9.6 | 66.0 | 24.4 |
|  | af | 340 | 390 | 0.7 | 0.5 | 10.9 | 73.9 | 15.2 |

(*)values corresponding to 45% conversion

EXAMPLE 22

Comparison of reference catalysts $A_o$ to $D_o$

Figure 4:
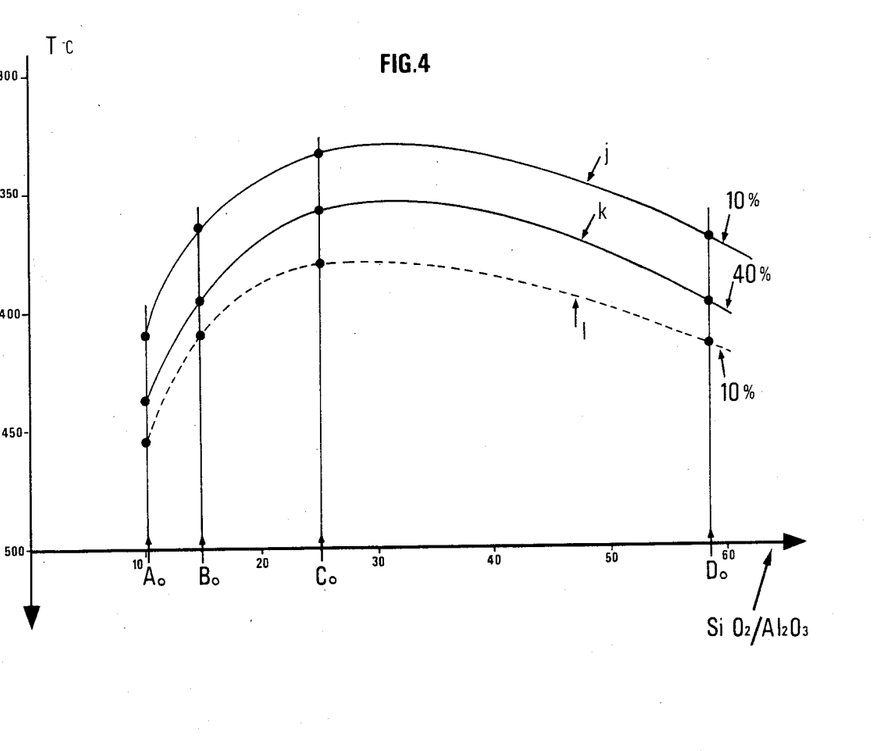
FIG. 4 shows the activities of catalysts $A_o$ to $D_o$ versus temperature for a 10% conversion (curves j and l) and for a 40% conversion (curve k). Curves j and k represent the activity of the catalysts before ageing. Curve 1 represents the activity of the catalysts after ageing.

The activities at low conversion (10%) and high conversion (40%) of catalysts $A_o$ to $D_o$ are compared in a temperature diagram versus the $SiO_2/Al_2O_3$ ratio $(T(°C.)=f(SiO_2/Al_2O_3))$ shown in FIG. 4.

Figure 5:
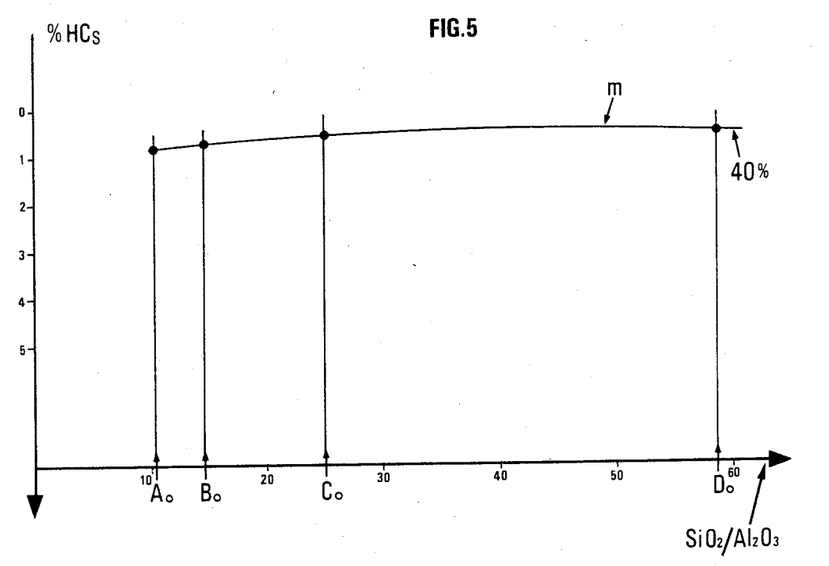
FIG. 5 shows the selectivities of catalysts $A_o$ to $D_o$ for a 40% conversion before ageng of the catalyst (curve m).

The selectivities at high conversion rate (40%) of catalysts $A_o$ to $D_o$ are plotted in a diagram of the percentage of formed saturated hydrocarbons versus the $SiO_2/Al_2O_3$ ratio $(\%(HC_s)=f(SiO_2/Al_2O_3))$ shown in FIG. 5.

Table 7, which shows the distribution of $C_1$ to $C_4$ gases, also provides informations on the selectivity.

The stability of the catalyst may be estimated in FIG. 4 by comparing the temperatures at which is obtained the 10% conversion before ageing of the catalyst (curve j) with those obtained after ageing (curve l).

The curve relative to a 40% conversion after ageing has not been shown in FIG. 4 in view of the difficulty to reach such a conversion with certain catalysts, particularly catalyst $A_o$ having a $SiO_2/Al_2O_3$ ratio of 10.6, the catalysts losing very quickly their activity versus time beyond 440°–450° C.

The following main points are thus made apparent:

The activity of catalysts $A_o$ to $D_o$ improve when the $SiO_2/Al_2O_3$ ratio increases from 10 to a value ranging between about 20 and 35 and then decreases for values higher than about 35, The selectivity is good for all the catalysts $A_o$ to $D_o$: the proportion of formed saturated products is always lower than 1%.

The formed $C_1$ to $C_4$ light hydrocarbons contain a small proportion of $C_1+C_2$. This proportion however becomes higher with a higher temperature.

TABLE 7

Percentages (by weight) of products and distribution of $C_1$ to $C_4$ light saturated hydrocarbons at high conversion rate (40%) for the catalysts $A_o$ to $D_o$ before ageing.

| CATALYSTS | % $C_4^-$ * | % $C_1 + C_2$ in $C_4^-$ | % $C_3$ in $C_4^-$ | % $C_4$ in $C_4^-$ |
|---|---|---|---|---|
| $A_o$ | 0.7 | 20.1 | 53.2 | 26.7 |
| $B_o$ | 0.6 | 14.2 | 60.7 | 25.1 |
| $C_o$ | 0.5 | 7.3 | 75.6 | 17.1 |
| $D_o$ | 0.5 | 12.8 | 68.6 | 18.6 |

* % $C_4^-$ by weight of the formed products.

EXAMPLE 23

Comparison of tin-containing catalysts L, N, O, P with $A_o$ to $D_o$, A to D and F to I catalysts The activities at low conversion (10%) and at high conversion (40%) of catalysts L, N, O and P are very slightly lower than those of the corresponding reference catalysts $A_o$ to $D_o$ having the same $SiO_2/Al_2O_3$ ratio. These slightly decreased activities result in a necessary increase of the temperatures by about 5° C., as compared with those used with catalysts $A_o$ to $D_o$, in order to obtain the desired conversion levels (10% or 40%).

As for reference catyalysts A to D, the stability of catalysts L, N, O and P could not be evaluated at high conversion rate (40%), these catalysts L, N, O and P losing too quickly their activity at high conversion, hence at high temperature.

The stability of catalysts L, N, O and P at 10% conversion is identical to that of the corresponding catalysts $A_o$, $B_o$, $C_o$, and $D_o$.

The selectivity at high conversion rate (40%) of catalysts L, N, O and P after ageing is very close to that of the corresponding reference catalysts $A_o$ to $D_o$: the production of saturated hydrocarbons does not differ by more than 0.1% from that of catalysts $A_o$ to $D_o$, the proportion of formed $C_1+C_2$ in the $C_4^-$ light gases is always slightly lower by an amount of about 2%.

The comparison of catalysts F to I according to the present invention shows that most of the activity and the stability of catalysts A to D is maintained and that the selectivity is clearly improved with respect to catalysts A to D.

Catalysts F to I have an activity and a stability clearly improved with respect to catalysts $A_o$ to $D_o$ and L, N, O and P respectively. The selectivity of catalysts F to I is very close to that of catalysts $A_o$ to $D_o$ and L, N, O and P respectively.

Catalysts F to I are, as a whole, superior to the comparison catalysts inasmuch as it is referred to the three basic properties of the catalysts: activity, stability and selectivity.

What is claimed as the invention is:

1. A process for the dismutation or transalkylation of alkylaromatic compounds, comprising subjecting said compounds to dismutation or transalkylation conditions, in the presence of a catalyst, wherein the catalyst contains:
(a) at least one acid mordenite whose total $SiO_2/Al_2O_3$ molar ratio is from about 12 to about 60 and whose sodium content is lower than 1% by weight,
(b) at least one metal selected from the group consisting of nickel, palladium and metals of group $I_B$ of the periodic classification of elements,
(c) at least one metal selected from the metals of group $IV_A$ of the periodic classification of elements.

2. A process according to claim 1 characterized in that the catalyst is prepared by introducing at least one metal from group $IV_A$ of the periodic classification of elements by means of an organic complex of this or these metals.

3. A process according to claim 1, wherein the acid mordenite contains less than 0.5% by weight of sodium.

4. A process according to claim 1, wherein the acid mordenite has a total $SiO_2/Al_2O_3$ molar ratio of about 20 to about 50.

5. A process according to claim 1, wherein the catalyst contains:
(a) from 30 to 99.9% by weight of acid mordenite,
(b) at least one metal selected from the group formed of nickel, palladium and silver,
(c) at least one metal from group $IV_A$ of the periodic classification of elements, selected from tin, lead and germanium.

6. A process according to claim 1, wherein the catalyst contains a binding agent selected from the group formed of clays, aluminas, silica and silica-aluminas.

7. A process according to claim 6, wherein the catalyst contains 3 to 50% by weight of binding agent.

8. A process according to claim 1, wherein the catalyst contains by weight:
(a) from 0.005 to 25% of at least one metal selected from the group formed of nickel, palladium and the metals of group $I_B$ of the periodic classification of elements,
(b) from 0.05 to 10% of at least one metal from group $IV_A$ of the periodic classification of elements.

9. A process according to claim 1, applied to toluene dismutation.

10. A process according to claim 1, applied to transalkylation of toluene and alkylaromatic hydrocarbons having at least 9 carbon atoms per molecule.

* * * * *